(12) United States Patent
Rafii et al.

(10) Patent No.: US 12,734,074 B2
(45) Date of Patent: Sep. 15, 2026

(54) CURVED CLIP DRESSING DEVICES AND METHODS OF USE

(71) Applicant: FXR LLC, Herndon, VA (US)

(72) Inventors: Shyaun Rafii, Herndon, VA (US); Andrew Falco, Alexandria, VA (US)

( * ) Notice: Subject to any disclaimer, the term of this patent is extended or adjusted under 35 U.S.C. 154(b) by 0 days.

(21) Appl. No.: 18/884,830

(22) Filed: Sep. 13, 2024

(65) Prior Publication Data

US 2026/0000549 A1 Jan. 1, 2026

Related U.S. Application Data

(60) Provisional application No. 63/664,767, filed on Jun. 27, 2024.

(51) Int. Cl.
*A61F 13/00* (2024.01)
*A61F 13/06* (2006.01)

(52) U.S. Cl.
CPC .. *A61F 13/066* (2013.01); *A61F 2013/00089* (2013.01)

(58) Field of Classification Search
CPC ....... A61B 17/685; A61B 17/86; A61B 17/84; A61F 2013/00089
USPC ........ 606/54
See application file for complete search history.

(56) References Cited

U.S. PATENT DOCUMENTS 4,728,323 A 3/1988 Matson
5,080,661 A * 1/1992 Lavender .......... A61F 13/00063 606/53
5,181,905 A 1/1993 Flam
5,447,492 A * 9/1995 Cartmell ............. A61F 13/0203 602/41
5,702,388 A * 12/1997 Jackson ............... A61B 17/685 606/151
6,194,629 B1 2/2001 Bernhard
8,216,288 B2 * 7/2012 Lee ....................... A61F 15/006 606/322
9,499,852 B2 11/2016 Jenkins et al.
9,730,696 B2 * 8/2017 Sanders, Jr. ........... A61B 17/08
10,695,237 B1 * 6/2020 Sanders, Jr. .......... A61F 15/006
2009/0318842 A1 12/2009 Kairinos
2009/0324883 A1 12/2009 Gray et al.
2013/0110025 A1 5/2013 Donnellan et al.
2017/0049628 A1 2/2017 Stevens
2018/0360667 A1 12/2018 Droche
2020/0253617 A1 8/2020 Williams
2023/0404811 A1 12/2023 Falco et al.

FOREIGN PATENT DOCUMENTS

WO WO-2022146850 A1 * 7/2022 ....... A61F 13/00063
WO WO-2024140975 A1 * 7/2024 ............ A61M 25/02

OTHER PUBLICATIONS

WO 2024/140975 A1 Translation (Year: 2024).*

(Continued)

*Primary Examiner* — Kim M Lewis
(74) *Attorney, Agent, or Firm* — Vorys, Sater, Seymour and Pease, LLP; Michael Messinger

(57) ABSTRACT

A clip is disclosed comprising a frame slidably positionable around a structure entering the skin of a patient and a layer to elute a fluid to the skin based on the frame being slidably positioned around the structure.

16 Claims, 4 Drawing Sheets

(56) References Cited

OTHER PUBLICATIONS

International Search Report issued Mar. 15, 2022, in International Application No. PCT/US2021/064988.
Written Opinion issued Mar. 15, 2022, in International Application No. PCT/US2021/064988.
"External Fixators", GPC Medical Ltd., Accessed Dec. 28, 2020 (one page).
"External Fixation Device", Medline Plus, Accessed Dec. 28, 2020 (one page).
Non-Final Office Action issued Apr. 8, 2025, in U.S. Appl. No. 18/039,092, 16 pages.

* cited by examiner

CURVED CLIP DRESSING DEVICES AND METHODS OF USE

FIELD

The present disclosure relates to dressings and wound care, and, more particularly to circumferential wound site dressings.

BACKGROUND

External fixators are used to immobilize bones and hold them in a stable position for healing or recovery. Conventional external fixators use a stabilizing frame that can be placed around a bone or area of treatment. The stabilizing frame often requires one or more rings and support rods or struts, Aluminum, titanium, or stainless steel percutaneous pins or wires are inserted into bone that then connect externally to the stabilizing frame. The stabilizing frame and pins provide alignment forces to maintain fracture fragments in proper position during healing or recovery.

External fixators are utilized in circumstances where there is a poor soft tissue envelope or when internal fixation would be contraindicated (such as due to infection, poor bone quality, open wounds, and the like). External fixation pins extrude from the skin and connect to the external stabilizing frame. One of the main complications encountered with the use of external fixation devices are pin site infections. Pin site infections may be caused due to various factors, such as patient-specific physiology, surgical technique, pin design and configuration, post-operative cleaning techniques and frequency, and the like. These infections can endanger the patient, and also pose a significant burden on the healthcare industry. Pin site infections can be mitigated by application of antiseptic materials around the pin site, for example. Applications of these materials can be cumbersome and time consuming and many times fall off due to no real way to secure them or ineffective securing techniques. Moreover, currently available means to apply the antiseptic materials relies on the patient to perform the application and is often forgotten or otherwise ignored due to the difficulties of the application.

DESCRIPTION

In aspects of the present disclosure, curved clip pin dressing devices and methods are disclosed. Curved clip pin dressing devices and methods are described which overcome the above problems and provides further advantages and features. In various aspects, curved clip pin dressing devices and methods protect the pin site and can elute an antiseptic/antimicrobial fluid which may prevent or otherwise minimize microbial (e.g., bacterial) burden and infectious rate while simultaneously maintaining a stable fixation point as a dressing.

It is to be appreciated that while the curved clip dressing devices of the present disclosure are described with reference to external fixator pins and/or wires, the curved clip dressing devices may be used on any external (percutaneous) circumferential structure entering the skin and requiring a wound dressing, without limitation, such as catheter sites, for example. These percutaneous sites are referred to herein collectively as "circumferential wound sites."

Further aspects, features, and advantages of the disclosure, as well as the structure and operation of the various embodiments of the disclosure are described in detail below with reference to accompanying drawings.

BRIEF DESCRIPTION OF THE DRAWINGS

The accompanying drawings, which are incorporated into and constitute a part of this specification, illustrate one or more examples of aspects of the present disclosure and, together with the description of examples herein, serve to explain the principles and implementations of the embodiments. The drawings should not be viewed as exclusive configurations. The subject matter disclosed is capable of considerable modifications, alterations, combinations, and equivalents in form and function, as will occur to those skilled in the art and having the benefit of this disclosure.

DETAILED DESCRIPTION

Figure 1:
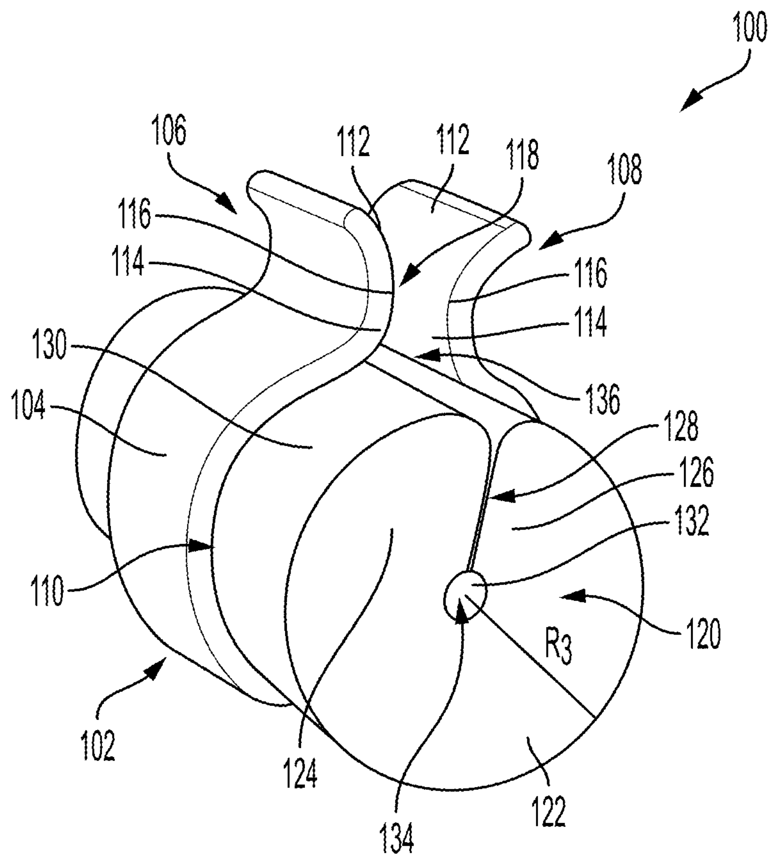
FIG. 1 is a curved clip dressing device, according to at least one aspect of the present disclosure.

In aspects of the present disclosure, curved clip dressing devices and methods are disclosed. In one or more aspects, a curved clip dressing device includes a frame and a layer, such as a wound dressing material or foam, and serves to protect a point of entry from bacteria and other elements found outside the body. For example, external fixation pins may be used to insert percutaneous pins from external to internal and attach to an external stabilizing frame, including but not limited to, providing alignment forces to maintain reduction of fracture fragments and deformity correction.

The following description is illustrative only and is not intended to be in any way limiting. Other aspects will readily suggest themselves to those of ordinary skill in the art having the benefit of this disclosure. Reference will be made in detail to implementations of the examples as illustrated in the accompanying drawings. The same reference indicators will be used to the extent possible throughout the drawings and the following description to refer to the same or like items.

In the description of example embodiments that follows, references to "one aspect", "an aspect", "an example aspect", "certain aspects," and the like, indicate that the aspect described may include a particular feature, structure, or characteristic, but every aspect may not necessarily include the particular feature, structure, or characteristic. Moreover, such phrases are not necessarily referring to the same aspect and such aspects may be combined with other aspects without limitation, unless otherwise stated. When a particular feature, structure, or characteristic is described in connection with a particular aspect, it is submitted that it is within the knowledge of one skilled in the art to effect such feature, structure, or characteristic in connection with other aspects whether or not explicitly described.

As used herein, the term "clip circumferential wound site dressing device" or simply "clip dressing device," and grammatical variants thereof, refers to a dressing that is positionable around a percutaneous circumferential wound site, such as a pin site for an external fixator or a catheter site, and the like, that provides microbial infection protection.

As used herein, the term "antimicrobial substance" or simply "antimicrobial," and grammatical variants thereof, refers to any substance that is able to destroy or inhibit the growth of microorganisms, including bacteria, fungus, virus, other pathogens, and the like, and any combination thereof. Examples of suitable antimicrobial substances include, but are not limited to, alcohol, peroxide, chlorhexidine, acetic acid, silver, an iodine (e.g., cadexomer iodine, providone-iodine such as BETADINE®, Avrio Health L.P., Stamford Forum), polyhexamethyl biguanide, sodium hypochlorite, VASHER (Byram Healthcare, White Plains, New York), PRONTOSAN® (B. Braun Medical Inc., Melsungen, Germany), other antimicrobial substances, and the like, and any combination thereof. In some aspects, the antimicrobial substance may be directly coated upon the clip or on a layer, such as an antimicrobial substance containing material, of the clip. As used herein, the term "coating" (also referred to as a film) refers to partial or complete coating of the clip, without limitation. In alternative or additional aspects, the antimicrobial substance may be contained within a material.

As used herein, the term "antimicrobial substance containing material," or simply "antimicrobial containing material," and grammatical variants thereof, refers to a biocompatible material comprising or capable of comprising (e.g., receiving) an antimicrobial substance. The material contains or is otherwise fed (e.g., from a cell containment opening) the antimicrobial substance for contact with a circumferential wound site (e.g., pin site wound) or otherwise allows elution of the antimicrobial substance to a circumferential wound site (e.g., pin site wound). For example, the antimicrobial containing material may comprise open cells (e.g., a foam) that receives and holds an antimicrobial substance in place for slow elution over time and while in use. Accordingly, the antimicrobial containing material need not initially contain the antimicrobial substance prior to its deployment to a circumferential wound site. Examples of suitable antimicrobial containing materials include, but are not limited to, biocompatible foam materials, hydrogel materials, hydrocolloid materials, alginate materials, and the like, and any combination thereof. Such materials may be biocompatible natural or synthetic polymers, such as polyurethane, silicone, gelatin, pectin, cellulose (e.g., carboxymethyl-cellulose, gauze (cotton)), guar gum, ADAPTIC™ (KCI USA, Inc., San Antonio, TX), or XEROFORM™ (Cardinal Health, Inc., Dublin, Ohio), and the like, and any combination thereof.

As used herein, the term "biocompatible adhesive," and grammatical variants thereof, refers to an adhesive used to adhere the antimicrobial containing material to the clip substrate directly or to an outer layer of material surrounding at least a portion, including all, of the clip substrate. Suitable biocompatible adhesives may include, but are not limited to, silicone adhesives, epoxide adhesives, acrylate adhesives (e.g., cyanoacrylate adhesives), and the like, and any combination thereof.

Figure 2:
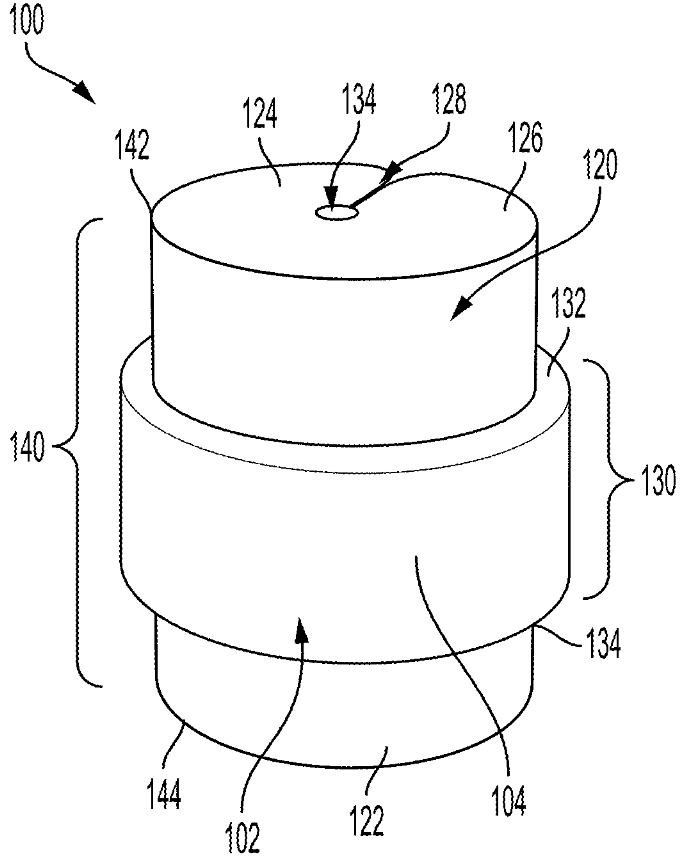
FIG. 2 is a top view of the curved clip dressing device of FIG. 1, according to at least one aspect of the present disclosure.

FIGS. 1 and 2 show a clip dressing device 100 (hereinafter "the clip 100") according to one or more aspects of the present disclosure. The clip 100 includes a frame 102 that defines an omega-like (Ω) shape. In some embodiments, the frame 102 is made of a polymer.

Figure 3:
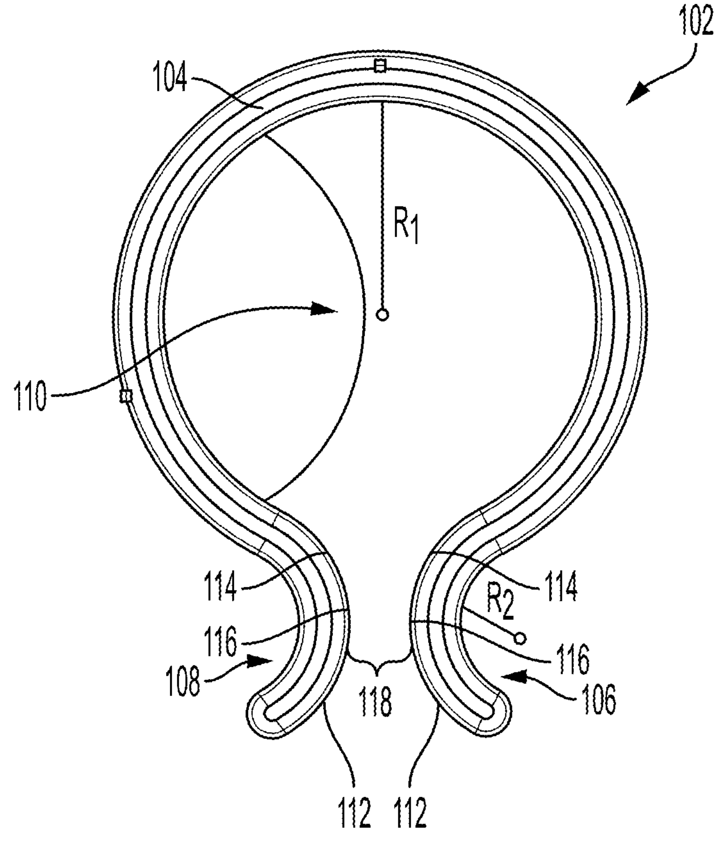
FIG. 3 is the frame of the curved clip dressing device of FIG. 1, according to at least one aspect of the present disclosure.

The frame 102 includes a curved frame body 104, a first frame arm 106 extending from a first side of the frame body 104, and a second frame arm 108 extending from a second side of the body 104 opposite the first side of the frame body 104. Referring briefly to FIG. 3, the frame body 104 defines a first radius of curvature $R_1$ and an opening 110. The first and second arms 106, 108 extend from the frame body 104 toward one another and then away from one another, defining the omega-like shape of the frame 102. The first and second arms 106, 108 each define a second radius of curvature $R_2$ as they extend toward one another and then subsequently away from one another. In some embodiments, as shown in FIG. 3, the first radius of curvature $R_1$ is greater than the second radius of curvature $R_2$. In some embodiments, the first radius of curvature $R_1$ is the same as the second radius of curvature $R_2$. In some embodiments, the first radius of curvature $R_1$ is less than the second radius of curvature $R_2$. The first and second arms 106, 108 each include a curved surface that includes an entrance cam portion 112, an exit cam portion 114, and an apex 116 defined at the transition of the entrance and exit cam portions 112, 114.

A gap 118 is defined between the apexes 116. The material of the frame 102 is selected such that the frame body 104 is sufficiently rigid, but capable of being flexed to transition the frame 102 between a first state in which the gap 118 is a first distance, and a second state in which the gap 118 is a second distance greater than the first distance. The frame 102 has a natural bias toward the first state such that, when a force is not applied to the frame 102 (i.e., a force that transitions the frame 102 toward the second state), the frame 102 is inclined to transition toward the first state.

In the first state, the gap 118 is less than the diameter of the structure to which that the clip 100 is to be coupled. In some embodiments, the gap 118 in the first state is less than the diameter of a percutaneous pin or a catheter, as examples. In the second state, the gap 118 is equal to, or at least substantially equal to, the diameter of the structure to which that the clip 100 is to be coupled. Accordingly, in the second state, the structure to which the clip 100 is to be coupled can pass between the arms 106, 108, such as into the opening 110.

The clip 100 further comprises a layer 120 positioned in the opening 110 of the frame 102. The frame 102 encompasses, or at least substantially encompasses the circumference of the layer 120. For instance, the frame 102 circumferentially encompasses the layer 120 except for at the gap 118. The layer 120 defines a tube-like shape having a layer body 122, a first layer arm 124 extending from a first side of the layer body 120, and a second layer arm 126 extending from a second side of the layer body 120 opposite of the first side of the layer body 120. As shown in FIG. 1, the layer body 122 confronts the frame body 104 and has a radius of curvature $R_3$ that matches, or at least substantially matches, the radius of curvature $R_1$ of the frame body 104. The first layer arm 124 extends from the layer body 122 along the frame body 104 toward the first frame arm 106 and the second layer arm 126 extends from the layer body 122 along the frame body 122 toward the second frame arm 108. The first and second layer arms 124, 126 abut one another and define a slot 128 therebetween that is aligned with the gap 118 defined by the first and second frame arms 106, 108. The frame 102 and the layer define a receiving area 136 that is situated between the slot 128 and the gap 118.

The layer 120 includes an outer layer surface 130 that confronts the frame body 104 and an inner layer surface 132 that defines a recess 134 extending through the layer 120. In some embodiments, the recess 134 has a diameter that is equal to, or substantially equal to, the diameter of the structure to which that the clip 100 is to be coupled. In some embodiments, the recess 134 has a diameter that is greater the diameter of the structure to which that the clip 100 is to be coupled. In some embodiments, the recess 134 has a diameter that is less the diameter of the structure to which that the clip 100 is to be coupled and the layer 120 is compliant such that the recess 134 can be expanded and conform to the diameter of the structure.

In some embodiments, the layer 120 comprises an antimicrobial containing material, such as foam or gauze, that is doped with, or otherwise includes, an antimicrobial substance. In some embodiments, the layer 120 is integral to the frame 102. In other embodiments, the layer 120 is coupled to the frame 102 using a biocompatible adhesive. In some embodiments, the layer 120 is removably couplable to the frame 102 such that the layer 120 can be replaced with another layer 120, which allows the frame 102 to be repeatably used.

As seen best in FIG. 1, the layer 120 can be relatively thick compared to the thickness of the frame 102 and thus can hold a sufficient quantity of antimicrobial substance for prolonged use. The particular thickness is not considered to be particularly limiting provided that the clip 100 can close around a circumferential wound site (e.g., pin site) without interfering with other elements, such as the frame of an external fixator device, as will be discussed in more detail below.

Referring to FIG. 2, the frame 102 has a frame width 130 that is defined by a distance between a first frame edge 132 and a second frame edge 134. The layer 120 has a layer width 140 that is defined by a first layer edge 142 and a second layer edge 144. In some embodiments, as shown in FIG. 2, the first layer edge 142 extends beyond the first frame edge 132 and the second layer edge 144 extends beyond the second frame edge 134 such that the layer width 140 is greater than the frame width 130. In some embodiments, the first layer edge 142 extends to the first frame edge 132 and the second layer edge 144 extends to the second frame edge 134 such that the frame width 130 is the same, or at least substantially the same, as the layer width 140. In some embodiments, only one of the first and second layer edges 142, 144 extends beyond the first and second frame edges 132, 134, respectively. In some embodiments, one or both of the first and second layer edges 142, 144 do not extend beyond the first and second frame edges 132, 134, respectively. In some embodiments, the layer width 140 is less than the frame width 130.

Figure 4:
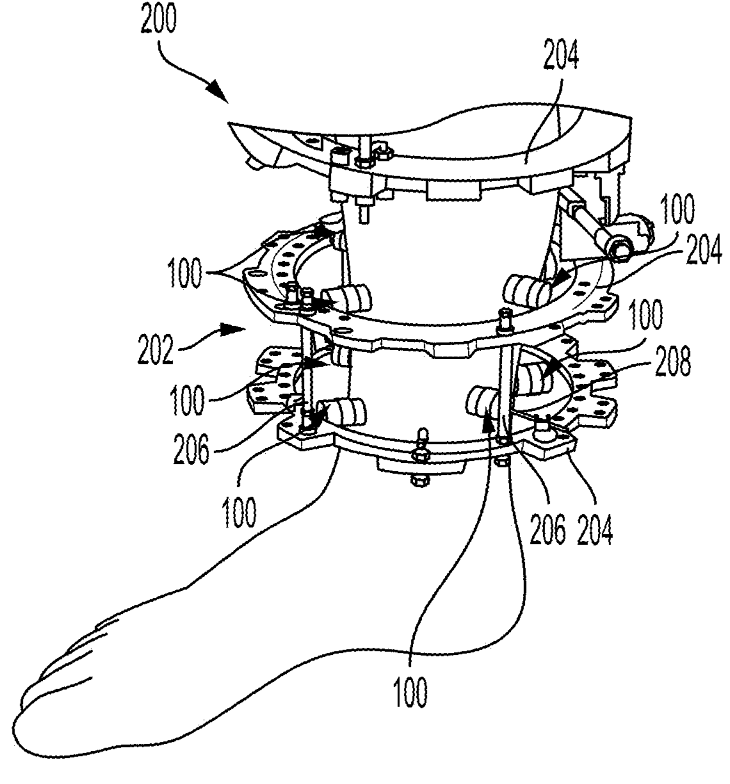
FIG. 4 is a plurality of curved clip dressing devices of FIG. 1 situated on percutaneous pins of an external fixature, according to at least one aspect of the present disclosure.

Referring now to FIG. 4, an example implementation of the clip 100 will now be described in connection with a patient's leg 200 that includes an external fixator 202 including a plurality of fixator rings 204, support rods 206 coupled to the fixator rings 204, and a plurality of percutaneous pins 208 (only one visible) extending from the fixator rings 204 into a patient's skin.

In use, a user grasps a clip 100 and aligns the gap 118 with a pin 208. The user then laterally moves clip 100 towards the pin 208 such that the entrance cam portions 112 of the first and second arms 106, 108 engage the pin 208. The user then applies a force to the clip 100 such that the pin 208 camming engages and slides along the entrance cam portions 112 of the first and second arms 106, 108, causing the first and second arms 106, 108 to move apart from one another, transitioning the frame 102 from the first state to the second state. Based on the pin 208 sliding past (surpassing) the apexes 116 of the first and second arms 106, 108, the first and second arms 106, 108 spring back toward one another, transitioning the frame 102 from the second state back toward the first state, capturing the pin 208 in the receiving recess 136 of the clip 100. The user then applies a force to the clip 100 such that the pin 208 slides within the slot 128 of the layer 120 and into the recess 134 of the layer 120, thereby coupling the clip 100 to the pin 208. Based on reaching this coupled state, the layer 120 can elute a fluid, such as an antimicrobial substance, to the location where the pin 208 enters the skin. FIG. 4 shows a plurality of clips 100 coupled to a plurality pins 208 in the above-described manner (only one pin 208 visible while the remainder are hidden by the clips 100 coupled thereto).

To remove a clip 100 from a pin 208, a user grasps the clip 100 and applies a force such that the pin 208 slides within the slot 128 of the layer 120 to the receiving recess 136. In this position, the user aligns the pin 208 with the gap 118 between the first and second frame arms 106, 108. The user then moves clip 100 away the pin 208 such that the exit cam portions 114 of the first and second arms 106, 108 engage the pin 208. The user then applies a force to the clip 100 such that the pin 208 camming engages and slides along the exit cam portions 114 of the first and second arms 106, 108, causing the first and second arms 106, 108 to move apart from one another, transitioning the frame 102 from the first state to the second state. Based on the pin 208 sliding past (surpassing) the apexes 116 of the first and second arms 106, 108, the clip 100 is released from the pin 208 and the first and second arms 106, 108 spring back toward one another, transitioning the frame 102 from the second state toward the first state.

The foregoing clip 100 provides numerous advantages that will be readily apparent to a person having ordinary skill in the art. As one example, the clip 100 is easily attachable to and detachable from an exterior structure, such as a percutaneous pin, by merely applying a force sufficient to slide the clip 100 relative to the structure in the above-described manner. The tube-like structure of the layer 120 and the frame arms 104, 106 ensure that the clip 100 will remain on the exterior structure unless a user actively grasps the clip 100 and applies a sufficient force along the line defined by the slot 128 and the gap 118.

In one or more aspects of the present disclosure, the layer may include first to third layers. The bottom (first) layer is a flexible slip resistant material configured to lie directly on a circumferential wound site. The second layer is a resilient flexible material that has a width wide arc. The third layer is a foam or sponge-like antimicrobial containing material configured to sit on the edge of the second layer abutting the skin, extending beyond the edge abutting the skin, or extending beyond both edges of the second layer (and thus first layer as well), and further substantially covering the entirety of the second layer. This serves as an all-encompassing, easy to apply dressing over percutaneous circumferential wound sites (e.g., pins for an external fixator). The clip dressing device described herein eliminates the process of having to individually uncoil dressing materials, submerging the dressing materials in a solution, and further individually coiling each circumferential wound site, all while ensuring the dressing does not loosen or move from the circumferential wound site. By gently sliding the clip dressing device along the desired circumferential would site, the clip fully encircles the circumferential wound site circumferentially, decreasing risk of infection, loosening of the dressing, all while providing an evenly distributed antibacterial zone surrounding the skin.

The various aspects of the clip dressing device described above are illustrative and not intended to be limiting. Further aspects and alternatives may be used in various examples, such as those described herein.

In one or more aspects, a clip dressing device has a clip which may be a combination of acid/base test strip (Litmus paper) with the antimicrobial containing material which would be in contact with the skin interface. One would be able to look at the litmus strip which is in contact with the skin interface, once this indicator changes color due to an acidic or basic environment one would have an idea of the bacterial burden, further individualizing the wound care regimen.

In one or more aspects, a package is provided with the frames separate from the layers and antimicrobial substance; the layers need not initially comprise the antimicrobial substance but may include it in other aspects, without departing from the present disclosure. The layers may be contained within a separator container and an applicator (e.g., foam with connecting bracket) may be integral with the layers or otherwise separate and used to attach the layers to the frames.

In one or more aspects, a layer has a material replacing the antimicrobial containing material and composed of a material which does not contain an antimicrobial substance but provides antimicrobial protection. This material may be any material comprising antimicrobial properties (e.g., antiseptic properties), but not limited to, gauze, ADAPTIC™ material, XEROFORM™ material.

In one or more aspects, and in addition to any of the above listed aspects alone or in combination, a slip resistant piece may be added to the layer 120 which would be in contact with the (e.g., pin site) itself. An advantage of the slip resistant piece would be to hold the entirety of the clip dressing device in its position more firmly and decrease the chances that it slips away from the skin edge.

In one or more aspects, the present disclosure solves a problem of wrapping a wound dressing around a circumferential wound site (e.g., pin site) which may be in close proximity to another circumferential wound site. A solution is provided which allows the clip to simply slide along the desired circumferential would site.

In one or more aspects, the clip may act as a place holder for a dressing that is wrapped around the external wound site. The clip itself would have no antimicrobial containing material or at least not one with loaded antimicrobial substance or an otherwise antimicrobial substance inherent to itself. The clip would slide around the circumferential wound site and secure a dressing which would already be wrapped around the skin at the circumferential wound site interface.

In a further feature, clip dressing devices may be combined in a self-contained package. In addition to serving as the dressing component, the frame may serve as the top of the package, whereas a layer comprised of an absorbent antimicrobial containing material may serve as the bottom and initially lacking an antimicrobial solution. The layer can be placed side down in a container with a shallow compartment that would allow for filling the compartment with an antibacterial/bactericidal solution to allow for the layer to be easily saturated prior to application; while the opposite edge would be facing upwards. There may be a covering overlying the edge facing opposite the shallow compartment, for example but not limited to, a wax adhesive that could easily be peeled off revealing the underlying product. Additionally, there would be breakable connections between each clip allowing for quick removal and application. Once the surrounding material is saturated by the solution, the clip can then be gently snapped into place around circumferential wound sites (e.g., external fixator pins) and mobilized to abut the skin, for example.

In this way, the present disclosure provides a unique way to protect a circumferential wound site and elute an antimicrobial fluid which may minimize the microbial (e.g., bacterial) burden and infectious rate while simultaneously maintaining a stable fixation point as a dressing.

Further advantages of clip dressing devices and methods described herein are quick and easy application compared to the traditional way of cutting material to size, submerging in antimicrobial solution(s), and application around the circumferential wound sites (e.g., pin sites) which can many times come loose. Clip dressing devices described here are more secure than conventional foam pads applied around circumferential wound sites that are not held on securely. Clip dressing devices also do not require a process of making a dressing individually for each individual site like some foam pad designs.

In this way, clip dressing devices may be a beneficial tool in any dressing regimen for any percutaneous circumferential wound sites, as defined herein, including external fixation as well as an external fixator kits due to ease of use, reduced time of application, and ability to secure itself against the circumferential wound site and to skin interface which would decrease irritation and theoretically decrease risk of site infection. Furthermore, increasing the amount of surface area in touch with the site-skin interface, as well as the surrounding areas, may result in a greater chance of decreasing site infections. In examples, the diameters of sites can range from about 1.6 millimeters (mm) to about 6.5 mm. The design of this product would be able to accommodate for all variations in sizes, including if there are smaller or larger circumferential wound site devices that are not yet utilized.

An additional benefit of this all in one, easy to apply type dressing goes hand in hand with the advancement of telehealth. With an increasing provider and patient population utilizing the technology of virtual health, this device would be an asset with dressing changes that do not take place in the office, as described above. Whether the patient, a family member, or home health be responsible for dressing changes, this process would no longer be left up to individual discretion of how to apply the dressing, but rather a predetermined consistent system.

The present disclosure provides, among others, the following examples, each of which may be considered as optionally including any alternative thereof.

Example 1. A clip comprising a frame slidably positionable around a structure entering the skin of a patient and a layer to elute a fluid to the skin based on the frame being slidably positioned around the structure.

Example 2. The clip of Example 1, wherein the frame comprises a first arm and a second arm. The frame is configurable between a first state in which a first distance is defined between the first arm and the second arm and a second state in which a second distance is defined between the first arm and the second arm. The second distance is greater than the first distance.

Example 3. The clip of Example 2, wherein the frame is transitionable toward the second state based on the structure engaging the first arm and the second arm as the frame is being slidably positioned around the structure.

Example 4. The clip of Examples 2 or 3, wherein the frame is naturally biased toward the first state.

Example 5. The clip of any one of Examples 1-4, wherein the frame defines an opening. The layer is positioned in the opening.

Example 6. The clip of Example 5, wherein the layer comprises a tube that defines a slot. The structure is slidable through the slot based on the frame being slidably positioned around the structure.

Example 7. The clip of Example 6, wherein the layer further defines a recess. The structure is positionable in the recess based on the frame being slidably positioned around the structure.

Example 8. The clip of any one of Examples 1-7, wherein the layer is comprised of foam.

Example 9. The clip of any one of Examples 1-8, wherein the fluid comprises an antimicrobial substance.

Example 10. The clip of any one of Examples 1-9, wherein the layer is coupled to the frame with an adhesive.

Example 11. The clip of any one of Examples 1-10, wherein the frame has a first width. The layer has a second width greater than the first width.

Example 12. A clip comprising a frame defining an opening and a layer positioned in the opening, wherein the layer defines a recess to slidably receive a structure entering skin of a patient, and wherein the layer is to elute a fluid to the skin based on the structure being received in the recess.

Example 13. The clip of Example 12, wherein the frame comprises a first arm and a second arm. The frame is configurable between a first state in which a first distance is defined between the first arm and the second arm and a second state in which a second distance is defined between the first arm and the second arm. The second distance is greater than the first distance. The structure is to engage the first arm and the second arm to transition the first arm and the second arm toward the second state based on the recess slidably receiving the structure.

Example 14. The clip of Example 13, wherein the frame is naturally biased toward the first state.

Example 15. The clip of any one of Examples 12-14, wherein the layer comprises a tube that defines a slot. The structure is slidable through the slot to reach the recess.

Example 16. A clip comprising a frame and a layer. The frame defines a gap. The frame is positionable around a structure entering skin of a patient defining a gap. The layer is to elute a fluid to the skin based on the frame being positioned around the structure. The frame is configurable between a first state in which the gap is a first length and a second state in which the gap is a second length greater than the first length. The structure is to cammingly engage the frame to transition the frame from the first state toward the second state.

Example 17. The clip of Example 16, wherein the frame is naturally biased toward the first state.

Example 18. The clip of Examples 16 or 17, wherein the frame further defines an opening. The layer is positioned in the opening.

Example 19. The clip of Example 18, wherein the layer comprises a tube that defines a slot. The structure is slidable through the slot based on the frame being positioned around the structure.

Example 20. The clip of Example 19, wherein the tube further defines a recess. The structure is positionable in the recess based on the frame being positioned around the structure.

One or more illustrative incarnations incorporating one or more elements are presented herein. Not all features of a physical implementation are described or shown in this application for the sake of clarity. It is understood that in the development of a physical embodiment incorporating one or more elements of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various aspects are described herein in terms of "comprising" various components, the aspects can also "consist essentially of" or "consist of" the various components.

Many alterations, modifications, and variations will be apparent to those skilled in the art in light of the foregoing description without departing from the spirit or scope of the present disclosure.

Therefore, the present disclosure is well adapted to attain the ends and advantages mentioned as well as those that are inherent therein. The particular examples and configurations disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A clip, comprising:

a frame slidably positionable around a structure entering skin of a patient; and a layer to elute a fluid to the skin based on the frame being slidably positioned around the structure, wherein the frame has a first width, and wherein the layer has a second width greater than the first width;

wherein the frame comprises a first arm and a second arm, and wherein the frame is configurable between:

a first state in which a first distance is defined between the first arm and the second arm; and a second state in which a second distance is defined between the first arm and the second arm, wherein the second distance is greater than the first distance; and wherein the structure is to cammingly engage the frame to transition the frame from the first state toward the second state.

2. The clip of claim 1, wherein the frame is naturally biased toward the first state.

3. The clip of claim 1, wherein the frame defines an opening, and wherein the layer is positioned in the opening.

4. The clip of claim 3, wherein the layer comprises a tube that defines a slot, and wherein the structure is slidable through the slot based on the frame being slidably positioned around the structure.

5. The clip of claim 4, wherein the layer further defines a recess, and wherein the structure is positionable in the recess based on the frame being slidably positioned around the structure.

6. The clip of claim 1, wherein the layer is comprised of foam.

7. The clip of claim 1, wherein the fluid comprises an antimicrobial substance.

8. The clip of claim 1, wherein the layer is coupled to the frame with an adhesive.

9. The clip of claim 1, wherein:
- the frame includes a first frame edge and a second frame edge that co-operatively define the first width;
- the layer includes a first layer edge and a second layer edge that co-operatively define the second width;
- the first layer edge extends beyond the first frame edge; and
- the second layer edge extends before beyond the second frame edge.

10. A clip, comprising:
- a frame defining an opening; and
- a layer positioned in the opening, wherein the layer defines a recess to slidably receive a structure entering skin of a patient, and wherein the layer is to elute a fluid to the skin based on the structure being received in the recess;
- wherein the frame comprises a first arm and a second arm, and wherein the frame is configurable between:
  - a first state in which a first distance is defined between the first arm and the second arm; and
  - a second state in which a second distance is defined between the first arm and the second arm, wherein the second distance is greater than the first distance; and
- wherein the structure is to cammingly engage the frame to transition the frame from the first state toward the second state.

11. The clip of claim 10, wherein the frame is naturally biased toward the first state.

12. The clip of claim 10, wherein the layer comprises a tube that defines a slot, and wherein the structure is slidable through the slot to reach the recess.

13. A clip, comprising:
- a frame defining a gap, wherein the frame is positionable around a structure entering skin of a patient; and
- a layer to elute a fluid to the skin based on the frame being positioned around the structure;
- wherein the frame is configurable between:
  - a first state in which the gap is a first length; and
  - a second state in which the gap is a second length greater than the first length;
- wherein the frame is naturally biased toward the first state; and
- wherein the structure is to cammingly engage the frame to transition the frame from the first state toward the second state.

14. The clip of claim 13, wherein the frame further defines an opening, and wherein the layer is positioned in the opening.

15. The clip of claim 14, wherein the layer comprises a tube that defines a slot, and wherein the structure is slidable through the slot based on the frame being positioned around the structure.

16. The clip of claim 15, wherein the tube further defines a recess, and wherein the structure is positionable in the recess based on the frame being positioned around the structure.

* * * * *